United States Patent [19]

Cassandrini et al.

[11] 4,263,434
[45] Apr. 21, 1981

[54] PIPERIDYL-TRIAZINE DERIVATIVES

[75] Inventors: Paolo Cassandrini, Bologna; Antonio Tozzi, Sasso Marconi, both of Italy

[73] Assignee: Chimosa Chimica Organica S.p.A., Pontecchio Marconi, Italy

[21] Appl. No.: 901,242

[22] Filed: Apr. 28, 1978

Related U.S. Application Data

[62] Division of Ser. No. 699,163, Jun. 23, 1976, Pat. No. 4,108,829.

[30] Foreign Application Priority Data

Dec. 18, 1975 [IT] Italy .................. 52769 A/75

[51] Int. Cl.³ .......................................... C07D 401/14
[52] U.S. Cl. ...................................... 544/198; 544/194; 544/196; 544/197; 544/204; 544/209; 544/210; 544/211; 544/212; 544/213; 544/218; 544/219; 260/45.8 NT; 260/45.8 A; 260/45.8 N
[58] Field of Search ....................... 544/198, 209, 212

[56] References Cited

U.S. PATENT DOCUMENTS

| 3,755,322 | 8/1973 | Winter et al. ............... 544/198 X |
| 3,883,523 | 5/1975 | Parton ............................ 544/198 X |
| 3,925,376 | 12/1975 | Chalmers et al. ............ 544/198 X |
| 3,928,344 | 12/1975 | Westlinning et al. ........ 544/198 X |

FOREIGN PATENT DOCUMENTS 1017862 1/1966 United Kingdom ................ 544/198

Primary Examiner—Joseph Paul Brust
Attorney, Agent, or Firm—Cushman, Darby & Cushman

[57] ABSTRACT

Novel piperidyl triazine derivatives are produced by reacting a substituted halogentriazine with a polyalcohol, a polymercaptan or a polyamine. The compounds are valuable light stabilizers for synthetic polymers, such as polyolefins, and fast to extraction in aqueous surfactant solutions.

9 Claims, No Drawings

PIPERIDYL-TRIAZINE DERIVATIVES

This is a division of application Ser. No. 699,163, filed June 23, 1976, now U.S. Pat. No. 4,108,829, issued Aug. 22, 1978.

BACKGROUND OF THE INVENTION

1. Field of the Invention

The present invention relates to novel piperidyltriazine derivatives which are useful for improving the stability to light, heat and oxidation of polymeric substances.

2. Description of the Prior Art

It is known that synthetic polymers are liable to undergo a severe deterioration of their physical and chemical properties when they are exposed to sunlight or other ultraviolet light source.

In order to improve the stability to light of said synthetic polymers, various stabilizers have been proposed, some of which have found a wide commercial acceptance in the field, such as some benzophenones, benzotriazoles, aromatic salicylates, α-cyanoacrylic acid esters, organo-tin compounds and the like, which although having a certain efficiency level, are not successful to solve the problem completely.

It is further known that some piperidine derivatives of 1,3,5-triazine can be used to protect a polymeric material from degradation due to ultraviolet light.

In particular, French Pat. No. 2181 059 describes triazine compounds having the general formula

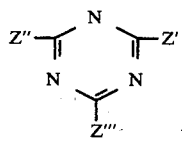

wherein $Z'$, $Z''$, $Z'''$ can be, among others, piperidine radicals of type

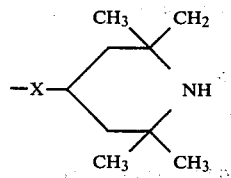

in which X is —O— or —NH—.

The above products considerably improve the light stability of polyolefins, but they are of poor utility in the application to an article of small thickness, such as fibers and films, inasmuch as they tend to be extracted by contact with water or aqueous solutions of surfactants, the stabilizer amount remaining in the polymer being no longer sufficient to provide the required light stabilization.

On the other hand the usual commercial light stabilizers, such as benzophenone derivatives, have a reduced effect on light stabilization in polyolefins, when used in articles of small thickness, such as fibers and films.

Therefore there is a need of more efficient light stabilizers for the protection against the polymer degradation due to UV light, as well as stabilizers fast to extraction from the polymer.

SUMMARY

An object of the invention is a novel class of piperidine derivatives of 1,3,5-triazine, useful as light stabilizers for polymers and characterized by an improved fastness to extraction from the polymer in the contact with an aqueous surfactant solution.

The triazine compounds of this invention have the following general formula (I):

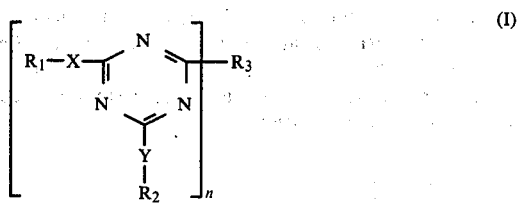

wherein $R_1$, $R_2$ same or different are hydrogen, hydroxyl, a straight or branched chain $C_1$ to $C_{18}$ alkyl, a $C_5$ to $C_{18}$ cycloalkyl, a substituted or not substituted $C_6$ to $C_{18}$ aryl, a $C_7$ to $C_{18}$ aralkyl, or a piperidine radical of formula (II)

in which $R_4$, $R_5$, $R_7$, $R_8$ same or different, are each a $C_1$ to $C_6$ alkyl and $R_6$ is H, O, a $C_1$ to $C_{12}$ alkyl, a $C_2$ to $C_{12}$ alkenyl or alkinyl;

$R_1$, $R_2$ can also represent a group

in which $R_9$, $R_{10}$ same or different, are each hydrogen, $C_1$ to $C_8$ alkyl, $C_5$ to $C_8$ cycloalkyl or $C_6$ to $C_8$ aryl;

X, Y same or different represent —O—, —S—,

$R_{11}$ being H, a straight or branched chain $C_1$ to $C_{18}$ alkyl, $C_5$ to $C_{18}$ cycloalkyl, $C_6$ to $C_{18}$ aryl, $C_7$ to $C_{18}$ aralkyl, or a piperidine radical of formula (II).

The radicals $R_1$—X—, $R_2$—Y—, taken as a single substituent group, can also be radicals from nitrogenous heterocyclic compounds having 5 to 8 members, linked to the triazine ring by a bisubstituted nitrogen atom of said radical.

They can also represent Cl— or Br—;

n is an integer from 2 to 6;

$R_3$ is a n-valent residue derivating from a polyalcohol, a polymercaptan or a polyamine by reaction of the active H atoms thereof with a halogen atom of a monohalogen triazine;

$R_3$ can be a radical of type $R_{12}-(Z)_n-$, wherein $R_{12}$ is a n-valent, $C_1$ to $C_{18}$ aliphatic, $C_5$ to $C_{18}$ cycloaliphatic or $C_6$ to $C_{18}$ aromatic radical, and Z is $-O-$, $-S-$,

wherein $R_{11}$ has the same meaning as previously indicated.

When n=2, the radical $R_3$ can also be the bivalent radical of a nitrogenous heterocyclic compound having 6 to 8 members, the bisubstituted nitrogen atoms of which are linked to a triazine ring; when n=2, $R_3$ can also be a radical of type

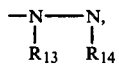

in which $R_{13}$, $R_{14}$, same or different, are each hydrogen, $C_1$ to $C_{12}$ alkyl, $C_5$ to $C_{12}$ cycloalkyl, $C_6$ to $C_{12}$ aryl, $C_7$ to $C_{12}$ aralkyl or a piperidine radical of formula (II).

When n=3, 4, 5, 6, $R_3$ can also be a radical of type

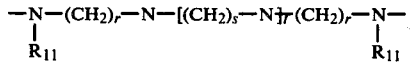

in which $R_{11}$ has the same meaning as previously indicated; r, s, same or different, are an integer from 2 to 6 and t is an integer from 0 to 3.

In formula (I) there is the condition that at least in one of the radicals $R_1-X-$, $R_2-Y-$ and $R_3$, at least one piperidine radical of formula (II) be present.

An additional object of the invention is to provide a method for the preparation of the above compounds of formula (I).

A further object of the invention is to provide a new stabilizer for synthetic polymers for improving their stability to light heat and oxidation.

A further object of the invention is to provide a composition of material comprising a synthetic polymer and an amount of stabilizer of formula (I) effective to improve the light stability thereof, as well as additional optional additives.

THE DETAILED DESCRIPTION

In accordance with this invention, in a piperidyltriazine of formula (I), the following preferred embodiments are intended for the various substituent groups:

Representatives of $R_1$, $R_2$ are H, OH, $NH_2$, $N(CH_3)_2$, methyl, ethyl, isopropyl, n-butyl, isobutyl, n-hexyl, n-octyl, n-dodecyl, n-octadecyl, cyclohexyl, 3,3,5-trimethylcyclohexyl, phenyl, o-, m-, p-toluyl, 2,6-dimethylphenyl, 2,4,6-trimethylphenyl, α- or β-naphthyl, benzyl, p-methylbenzyl, 2,2,6,6-tetramethyl-4-piperidyl, 1,2,2,6,6-pentamethyl-4-piperidyl, 1-allyl-2,2,6,6-tetramethyl-4-piperidyl.

Representatives of $R_{11}$ are hydrogen, methyl, ethyl, n-butyl, isobutyl, n-hexyl, n-octyl, n-dodecyl, n-octadecyl, cyclohexyl, 3,3,5-trimethylcyclohexyl, phenyl, p-toluyl, benzyl, 2,2,6,6-tetramethyl-4-piperidyl, 1,2,2,6,6-pentamethyl-4-piperidyl, 1-propyl-2,2,6,6-tetramethyl-4-piperidyl.

Representatives of radicals $R_1-X-$, $R_2-Y-$when they represent radicals of nitrogenous heterocyclic compounds having 5 to 8 members, are 1-pyrrolidinyl, 1-piperidinyl, 4-morpholinyl, 4-methyl-1-piperazinyl, 4-methyl-1-homopiperazinyl.

Representatives of $R_{12}$ are, when n=2; methylene, ethylene, 1,2-propylene, trimethylene, hexamethylene, 2,2,4-trimethylhexamethylene, 2,4,4-trimethylhexamethylene, decamethylene, 1,4-cyclohexylene, 4,4'-methylenedicyclohexylene, o-, m-, p-phenylene, o-, m, p-xylylene.

When n=3, examples of $R_{12}$ are:

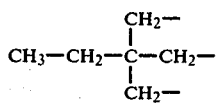 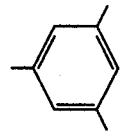

When n=4, examples of $R_{12}$ are:

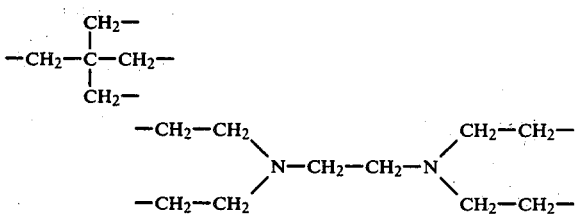

When n=2, radical $R_3$ can also be a radical of a heterocyclic compound having 6 to 8 members containing 2 nitrogen atoms, such as:

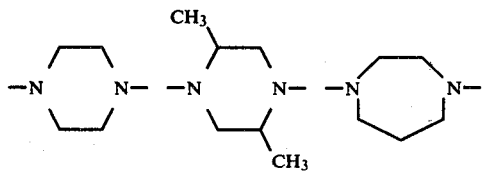

or it can be substituted by a hydrazine radical such as

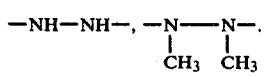

When n=3, radical $R_3$ can be a radical from a dialkylenetriamine, such as:

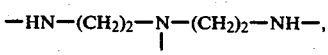

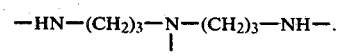

When n=4, radical $R_3$ can be a radical from a trialkylenetetramine, such as:

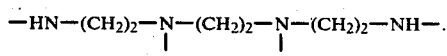

When n=5, radical $R_3$ can be a radical from a tetraalkylenepentamine, such as:

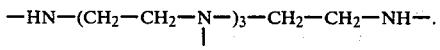
$$-HN-(CH_2-CH_2-N-)_3-CH_2-CH_2-NH-.$$

When n=6, radical $R_3$ can be a radical from a pentaalkylenehexamine, such as:

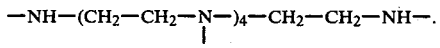
$$-NH-(CH_2-CH_2-N-)_4-CH_2-CH_2-NH-.$$

Preparation

The triazine compounds of formula (I) can be prepared by reacting a 4,6-bisubstituted 2-halogen 1,3,5-triazine of formula

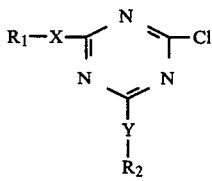
(III)

with a polyfunctional compound of formula

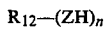
$R_{12}-(ZH)_n$ (IV)

or with a hydrazine of formula

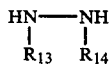
(V)

or with a polyamine of formula

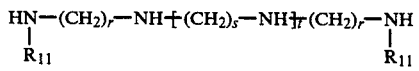
(VI)

The molar ratio of the reactants of formula (III) to the reactants of formula (IV) is preferably n:1, the molar ratio of the reactants of formula (III) to the reactants of formula (V) is 2:1; the molar ratio of the reactants of formula (III) to the reactants of formula (VI) is preferably one mole of (III) per one amine group; in each case it is possible to employ the reactant of formula (III) in excess to assure a complete reaction.

An alternative process for the preparation of compounds of formula (I) comprises reacting a 6-substituted 2,4-dichloro-1,3,5-triazine of formula

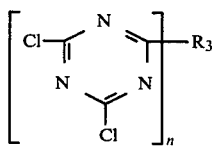
(VII)

with compounds having the formula $R_1-XH, R_2-YH:$ (VIII)

In such a case the molar ratio of reactants (VIII) to dichlorotriazine (VII) is 2n:1, but it is possible to employ an excess of reactants $R_1-XH$, $R_2-YH$ to assure a complete reaction.

The reactions of halogentriazines (III) or (VII) with the compounds of formula (IV), (V), (VI), (VIII) respectively are carried out preferably in the presence of inert solvents such as acetone, dioxane, toluene, xylene, generally operating at the boiling temperature of the solvents.

The reactions are carried out in the presence of organic or inorganic bases in order to fix hydrogen halide; there can be used for example: triethylamine, or tributylamine; sodium hydroxide; carbonate or bicarbonate; potassium hydroxide or carbonate; sodium alcoholates in the case that the compounds of formula (IV) or formula (VIII) are alcohols; sodium mercaptides in the case that the reactants of formula (IV) or formula (VIII) are mercaptans; it is also possible to use an amine excess in the case that a product of formula (VII) is reacted with compounds of formula (VIII) in which X, Y represent

$$-N-.$$
$$\phantom{-}R_{11}$$

In order to further illustrate the present invention, some examples of preparation are given in the following for an illustrative and not limitative purpose.

EXAMPLE 1

(A) 2-chloro-4,6-bis(2,6-dimethylphenoxy)-1,3,5-triazine was prepared according to the teachings of German patent application No. 2307 777.

To 55.3 g (0.3 moles) of cyanuric chloride dissolved in 300 ml of acetone were added within 30 minutes at 20°-25° C. a solution of 73.2 g (0.6 moles) of 2,6 dimethylphenol, 24 g (0.6 moles) of sodium hydroxide and 340 ml of water.

The mixture was stirred for three hours at the same temperature and the precipitate so obtained was removed by filtration, washed, dried and crystallized from petroleum ether: a white powder melting at 159°-160° C. was obtained.

(B) Preparation of N,N'-bis(2,2,6,6-tetramethyl-4-piperidyl)-N,N'-bis[2,4-bis(2,6-dimethylphenoxy)-1,3,5-triazin-6-yl]hexamethylene diamine.

35.5 g (0.1 mole) of 2-chloro-4,6-bis(2,6-dimethylphenoxy)-1,3,5-triazine, 19.7 g (0.05 moles) of 1,6-bis(2,2,6,6-tetramethyl-4-piperidylamino)hexane, 4 g (0.1 mole) of sodium hydroxide and 250 ml of xylol were boiled for 16 hours under stirring. The reaction solvent was removed, the residue was washed with water, dried at 100° C./1 mm and crystallized from anhydrous ethanol.

A white solid melting at 224°-229° C., N %=13.34 (calculated for $C_{62}H_{84}N_{10}O_4$=13.55%) was obtained.

EXAMPLE 2

(A) 2-chloro-4,6-bis(2,2,6,6-tetramethyl-4-piperidylamino)-1,3,5-triazine was prepared according to the French Pat. No. 2181 059:

To 18.45 (0.1 mole) cyanuric chloride, slurried into 600 ml water, were added 31.2 g (0.2 moles) of 4-amino-2,2,6,6-tetramethylpiperidine and a solution of 8 g (0.2 moles) of sodium hydroxide in 20 ml water. The mixture was stirred for 30 minutes at room temperature, then it was heated to 90° C. for 16 hours.

After cooling, the precipitate was removed by filtration, washed and dried under vacuum. A white powder melting at 277°-278° C. was obtained.

Preparation of
(B) N,N'-bis[2,4-bis(2,2,6,6-tetramethyl-4-piperidylamino)-1,3,5-triazin-6-yl]hexamethylenediamine:

42.3 (0.1 mole) of 2-chloro-4,6-bis(2,2,6,6-tetramethyl-4-piperidylamino)-1,3,5-triazine, 5.8 g (0.05 moles) of hexamethylenediamine, 4 g (0.1 moles) of sodium hydroxide and 500 ml of xylene were boiled for 16 hours under stirring. After removing the reaction solvent, the residue was washed with water, dried at 100° C./1 mm and crystallized from methylethylketone.

A white solid melting at 153°–156° C. was obtained. N % = 24.66 (calculated for $C_{48}H_{90}N_{16}$ = 25.16%).

EXAMPLE 3

(A) Preparation of 2-chloro-4,6-bis-(n-butylamino)-1,3,5-triazine as starting compound:

To a mixture of 18.45 g (0.1 mole) of cyanuric chloride, 180 ml of acetone and 160 g of ice was added 14.6 (0.2 moles) of n-butylamine dissolved in 100 ml acetone. The mixture temperature was raised to 30° C., then 8 g (0.2 moles) of sodium hydroxide dissolved in 100 ml of water were added.

The mixture was stirred for 6 hours at 30°–35° C., then the precipitate so obtained was filtered, washed with water and dried on anhydrous $CaCl_2$. A white powder melting at 209°–212° C. was obtained, chlorine % = 13.70 calculated for $C_{11}H_{20}ClN_5$ = 13.81%.

(B) Preparation of N,N'-bis(2,2,6,6-tetramethyl-4-piperidyl)-N,N'-bis[2,4-bis-(n-butylamino)-1,3,5-triazin-6-yl]ethylene diamine:

51.5 (0.2 moles) of 2-chloro-4,6-bis-n-butylamino-1,3,5-triazine, 33.8 g (0.1 mole) of 1,2-bis(2,2,6,6-tetramethyl-4-piperidylamino)ethane, 8 g (0.2 moles) of sodium hydroxide and 500 ml of xylene were boiled for 16 hours under stirring. After removing the reaction solvent, the residue was washed with water, dried at 100° C./1 mm and crystallized from methyl-ethylketone.

A white solid melting at 143°–45° C. was obtained. N % = 24.51 (calculated for $C_{42}H_{80}N_{14}$ = 25.12%).

EXAMPLE 4

Preparation of N,N'-bis(2,2,6,6-tetramethyl-4-piperidyl)-N,N'-bis-[2,4-bis(2,2,6,6-tetramethyl-4-piperidylamino)-1,3,5-triazin-6-yl]ethylenediamine.

21.15 g (0.05 moles) of 2-chloro-4,6-bis(2,2,6,6-tetramethyl-4-piperidylamino)-1,3,5-triazine (prepared according to example 2A), 8.45 g (0.025 moles) of 1,2-bis-(2,2,6,6-tetramethyl-4-piperidylamino)ethane, 2 g 0.05 of sodium hydroxide and 150 ml of xylene were boiled for 16 hours under stirring. After removing the reaction solvent, the residue was washed with water, dried at 100° C./1 mm and crystallized from benzene.

A white solid melting at 325°–328° C. was obtained. N % = 22.14 (calculated for $C_{62}H_{116}N_{18}$ = 22.66%).

EXAMPLE 5

Preparation of N,N'-bis[2,4-bis(2,2,6,6-tetramethyl-4-piperidylamino)-1,3,5-triazin-6-yl]ethylenediamine.

42.3 (0.1 mole) of 2-chloro-4,6-bis(2,2,6,6-tetramethyl-4-piperidylamino)-1,3,5-triazine (prepared according to example 2A), 3 g (0.05 moles) of ethylenediamine, 4 g of sodium hydroxide and 150 ml of xylene were boiled for 16 hours under stirring.

After removing the reaction solvent, the residue was washed with water, dried at 100° C./1 mm and crystallized from methanol. A white solid melting at 290°–292° C. was obtained. N % = 26.09 (calculated for $C_{44}H_{82}N_{16}$ = 26.83).

EXAMPLE 6

(A) Preparation of N,N'-bis(2,4-dichloro-1,3,5-triazin-6-yl)piperazine.

To 36.9 (0.2 moles) of cyanuric chloride dissolved in 200 ml of acetone was added with a solution of 8.6 g (0.1 mole) of anhydrous piperazine in 50 ml of acetone at 0°–5° C. within 30 minutes. It was stirred for 30 minutes at 0°–5° C., then a solution of 8 g (0.2 moles) of NaOH in 50 ml of water were added within 30 minutes at the same temperature. It was stirred again for 4 hours at 0°–5° C., then it was diluted with 100 ml of ice water, filtered, washed with water and dried on anhydrous $CaCl_2$. A white powder melting at >300° C. was obtained, chlorine % 37.32 (calculated for $C_{10}H_8Cl_4N_8$ = 37.17%).

(B) Preparation of N,N'-bis[2,4-bis[N(2,2,6,6-tetramethyl-4-piperidyl)-n-butylamino]-1,3,5-triazin-6-yl]piperazine.

19.1 g (0.05 moles) of N,N'-bis(2,4-dichloro-1,3,5-triazin-6-yl)piperazine, 46.6 g (0.22 moles) of 2,2,6,6-tetramethyl-4-(n-butyl-amino)piperidine, 80 ml of xylene and 8 g (0.2 moles) of NaOH were heated at reflux temperature for 16 hours. After removing the reaction solvent, the residue was washed with water, dried at 100° C./1 mm and crystallized from methylethylketone.

A white crystalline product melting at 272°–275° C. was obtained, N % 20.37 (calculated for $C_{62}H_{116}N_{16}.H_2O$ = 20.32%).

EXAMPLE 7

(A) Preparation of 2-chloro-4,6-bis-[N-ethyl-2,2,6,6-tetramethyl-4-piperidyl-amino]-1,3,5-triazine.

To a mixture of 92.2 g (0.5 moles) of cyanuric chloride, 500 ml of acetone and 160 g of ice was added 184 g (1 mole) of 2,2,6,6-tetramethyl-4-ethylaminopiperidine dissolved in 100 ml of acetone.

The mixture temperature was raised to 35° C., then 40 g (1 mole) of sodium hydroxide dissolved in 100 ml of water were added. The mixture was stirred for 6 hours at 35°–40° C., then the precipitate so obtained was filtered, washed with water and dried on anhydrous $CaCl_2$. After crystallization from acetone a white crystalline powder melting at 127°–129° C. was obtained, chlorine % = 7.36 (calculated for $C_{25}H_{46}ClN_7$ = 7.40).

(B) Preparation of N,N',N''-tris[2,4-bis[N-ethyl-2,2,6,6-tetramethyl-4-piperidylamino]1,3,5-triazin-6-yl]-diethylenetriamine.

143.8 g (0.3 moles) of 2-chloro-4,6-bis-[N-ethyl-2,2,6,6-tetramethyl-4-piperidylamino]-1,3,5-triazine, 10.3 g (0.1 mole) of diethylenetriamine, 12 g of sodium hydroxide and 450 ml of xylene were boiled for 16 hours under stirring.

After filtration, the solution was stirred at room temperature with 50 ml of water. A white precipitate, melting at 145°–150° C., was obtained. N % = 22.78 calculated for $C_{79}H_{148}N_{24}.H_2O$ = 23.13%).

LIGHT STABILIZATION TESTS

The piperidyl triazine derivatives of formula (I) are useful and valuable agents for improving the stability to light, heat and oxidation of synthetic polymers such as, for example, high and low density polyethylene, polypropylene, ethylene-propylene copolymers, ethylene-vinylacetate copolymers, polybutadiene, polyisoprene, polystyrene, styrene-butadiene copolymers, acrylonitrile-butadiene-styrene copolymers, vinyl- and vinylidene chloride polymers and copolymers, polyoxymethylene, polyethylene-terephthalate, nylon 66, nylon 6, nylon 12, polyurethanes, unsaturated polyesters.

The compounds of formula (I) can be employed in a mixture with the synthetic polymers in various proportions, depending on the polymer nature, final use and presence of additional additives.

Generally it is preferable to employ from 0.01 to 5% by weight of compounds of formula (I) referred to the polymer weight, more preferably from 0.1 to 1%.

The compounds of formula (I) can be included in a polymeric material composition by various procedures, such as dry mixing in the form of powder, or by a wet process in the form of a solution or slurry. In said operation the synthetic polymer can be employed in the form of powder, granulate, solution, slurry or emulsion.

The polymers stabilized by the products of formula (I) can be used for the manufacture of molded articles, films, tapes fibers, monofilaments and the like.

A mixture of compounds of formula (I) and synthetic polymers can be optionally additioned with other additives, such as antioxidants, UV absorbers, nickel stabilizers, pigments, charges, plastifying agents, antistatic agents, flame retardants, lubricating agents, anticorrosive agents, metal inhibitors, and the like.

Particular examples of additives which can be employed in a mixture with the compounds of formula (I) are:

phenolic antioxidants, such as 2,6-ditert-butyl-p-cresol, 4,4'-thiobis-(3-methyl-6-tertbutylphenol), 1,1,3-tris-(2-methyl-4-hydroxy-5-tertbutylphenyl)butane, octadecyl-3-(3,5-ditertbutyl-4-hydroxyphenyl)propionate, pentaerythritol-tetra-(3,5-ditert-butyl-4-hydroxyphenyl)propionate, tris-(3,5-ditert-butyl-4-hydroxybenzyl)isocyanurate;

esters of thiodipropionic acid, such as di-n-dodecyl-thiodipropionate, di-n-octadecyl-thiodipropionate, aliphatic sulfides and disulfides, such as di-n-dodecyl-sulfide, di-n-octadecyl-sulfide, di-n-octadecyl-disulfide;

aliphatic, aromatic or aliphatic-aromatic phosphites and thiophosphites, such as tri-n-dodecyl-phosphite, tris-(n-nonylphenyl)phosphite, tri-n-dodecyl-trithiophosphite, phenyl-di-n-decylphosphite, di-n-octadecyl-pentaerythritoldiphosphite;

UV absorbers such as 2-hydroxy-4-n-octyloxybenzophenone, 2-hydroxy-4-n-dodecyloxybenzophenone, 2-(2'-hydroxy-3',5'-ditert-butylphenyl)5-chlorobenzotriazole, 2-(2'-hydroxy-3',5'-di-tert-amylphenyl)benzotriazole, 2,4-ditertbutylphenyl-3,5-ditertbutyl-4-hydroxybenzoate, phenyl-salicylate, p-tert-butylphenyl-salicylate, 2,2'-dioctyloxy-5,5'-ditertbutyloxanilide, 2-ethoxy-5-tertbutyl-2'-ethyloxanilide;

nickel stabilizers such as Ni monoethyl-3,5-ditertbutyl-4-hydroxybenzylphosphonate, butylamine-Ni 2,2'-thiobis-(4-tertoctylphenolate) complex, Ni 2,2'-thiobis-(4-tertoxtylphenolphenolate), Ni dibutyldithiocarbamate, Ni 3,5-ditertbutyl-4-hydroxybenzoate, Ni complex of 2-hydroxy-4-n-octyloxybenzophenone; organotin compounds, such as dibutyl-tin-maleate, dibutyl-tin-laurate, di-n-octyl-tin-maleate;

acrylic esters, such as ethyl-α-cyano-β,β-diphenylacrylate, methyl-α-cyano-β-methyl-4-methoxycinnamate;

metal salts of higher fat acids, such as calcium, barium, zinc, cadmium, lead, nickel stearates, calcium cadmium, barium, zinc laurates.

In the following several examples are described, in an illustrative and not limitative way, for illustrating the usefulness of the compounds of formula (I) obtained in examples 1-7, for the stabilization of synthetic polymers.

The results of the tests are listed in the tables and compared with tests carried out without using any stabilizer and using a known stabilizer commercially available.

EXAMPLE 8

2.5 g of each of the compounds listed in table 1 below, dissolved in 100 ml chloroform, were mixed with 1000 g polypropylene (Moplen C, manufactured by Società Montedison, Italy), 1 g n-octadecyl-3(3,5-ditert.butyl-4-hydroxy-phenyl)propionate and 1 g calcium stearate.

The solvent was removed in an oven under vacuum at a temperature of 50° C. for 4 hours.

The dry mixture so obtained was then extruded at a temperature of 200° C. and made into granules, wherefrom 0.2 mm thick plates were produced by diecasting at 200° C.

Said plates were exposed in a Xenotest 150 apparatus at a black panel temperature of 60° C. and the increase in the content of carbonyl groups was periodically determined using the not exposed specimens for balancing the polymer original absorption. The time (T 0.1) required to have a $\Delta CO\% = 0.1$ at 5.85 μm was then calculated.

As a comparison, a polymer plate was produced under the same conditions, but without addition of any light stabilizer, and another one with the addition of 2.5 g of 2-hydroxy-4-n-octyloxybenzophenone, a usual commercial stabilizer.

The results are referred in Table 1.

TABLE 1

| Stabilizer | T 0.1 (hours) |
|---|---|
| None | 280 |
| 2-hydroxy-4-n-octyloxybenzophenone | 900 |
| Compound of example 1 | 1170 |
| Compound of example 2 | 1550 |
| Compound of example 3 | 1460 |
| Compound of example 4 | 1780 |
| Compound of example 5 | 1680 |
| Compound of example 6 | 1600 |
| Compound of example 7 | 1570 |

EXAMPLE 9

2 g of each of the compounds listed in table 2 below, dissolved in 100 ml chloroform, were mixed with 1000 g of high density polyethylene (Moplen RO, manufactured by Società Montedison, Italy), 0.5 g of n-octadecyl-3-(3,5-ditert.butyl-4-hydroxy-phenyl)propionate and 1 g of calcium stearate.

The solvent was removed in an oven under vacuum at a temperature of 50° C. for 4 hours.

The dry mixture so obtained was then extruded at a temperature of 190° C. and made into granules, wherefrom by diecasting at 200° C. plates 0.2 mm thick were produced, said plates were exposed in a Xenotest 150 apparatus, as in example 8.

The time T 0.05 required to have $\Delta CO\% = 0.05$ at 5.85 μm was determined.

As a comparison, under the same conditions a polymer plate was produced without addition of any light stabilizer and another plate was produced with addition of 2 g of 2-hydroxy-4-n-octyloxybenzophenone.

The results are referred in table 2.

TABLE 2

| Stabilizer | T 0.05 (hours) |
| --- | --- |
| None | 320 |
| 2-hydroxy-4-n-octyloxybenzophenone | 1100 |
| Compound of example 1 | 1750 |
| Compound of example 2 | 2300 |
| Compound of example 3 | 2080 |
| Compound of example 4 | 2360 |
| Compound of example 5 | 2210 |
| Compound of example 6 | 2190 |
| Compound of example 7 | 2270 |

EXAMPLE 10

The polypropylene granules produced in example 8 were made into fibers under the following conditions:

| Extruder temperature | 250–260° C. |
| --- | --- |
| Die temperature | 250° C. |
| Stretching ratio | 1:4 |
| Multifilament count | 1080/200 den |

The fibers were assembled on a white paperboard and exposed until brittleness in a Xenotest 150 at a black panel temperature of 60° C.

Another lot of the same fibers were subjected to tests of extraction fastness under the following conditions: the fibers fixed to a stainless steel frame were soaked into an aqueous solution containing 0.5% b.w. of a commercially available surfactant "DIXAN", under stirring at a temperature of 80° C.

After 10 hours treating, the fibers were rinsed with distilled water, dried and exposed until brittleness to the Xenotest 150 under the same conditions as above.

As a comparison under the same conditions, polypropylene fibers were produced and treated with addition of (a) 0.25% by weight of 2-hydroxy-4-n-octyloxybenzophenone, and (b) 0.25% by weight of 2,4,6-tris(2,2,6,6-tetramethyl-4-piperidylamino)1,3,5-triazine, as an example of French patent 2181 059. The results obtained are referred in table 3.

TABLE 3

| Stabilizer | Time to brittleness (hours) Not treated fibers | Time to brittleness (hours) Treated fibers |
| --- | --- | --- |
| (a) | 670 | 360 |
| (b) | 1080 | 380 |
| Compound of example 1 | 950 | 780 |
| Compound of example 2 | 1160 | 960 |
| Compound of example 3 | 1020 | 810 |
| Compound of example 4 | 1250 | 1040 |
| Compound of example 5 | 1090 | 870 |
| Compound of example 6 | 1170 | 920 |
| Compound of example 7 | 1190 | 870 |

From the test results, a considerable increase in the time required to induce a degradation in a polymer stabilized by the invention compounds can be observed with respect to the same polymer not stabilized.

Furthermore, clearly improved effects induced by the invention compounds can be observed in comparison with a similar proportion of a prior art additive.

It will be further appreciated from table 3 that the stabilizers of the invention maintain a very high proportion of their activity, when the stabilized fibers have been treated so as to promote the extraction thereof from the polymer, even when the polymer is in the very thin form of a fiber or film.

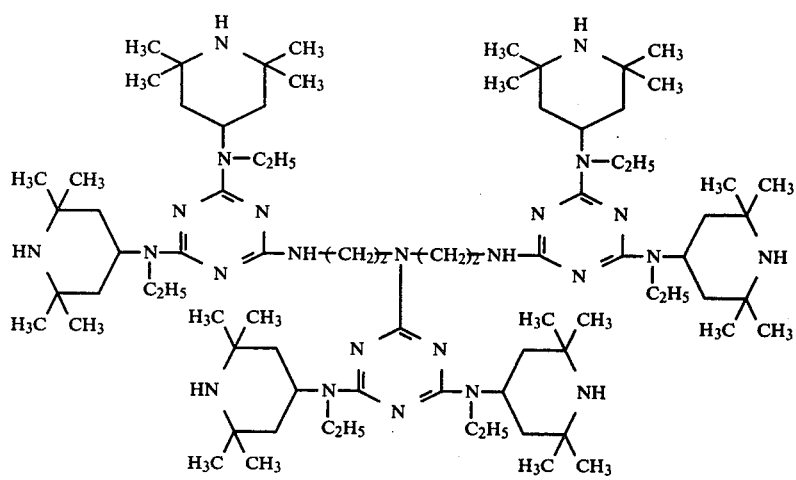

We claim:

1. A compound having the formula

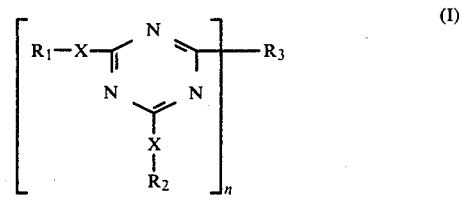

wherein:

$R_1$, $R_2$ same or different, are hydrogen, straight or branched chain $C_1$ to $C_{10}$ alkyl, $C_5$ to $C_{10}$ cycloalkyl, phenyl, phenyl substituted by 1 to 3 $C_1$–$C_4$ alkyls, or a piperidine radical of formula (II)

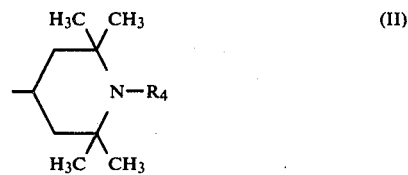

in which $R_4$ is hydrogen or $C_1$ to $C_4$ alkyl;

X is —O—,

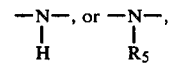

wherein $R_5$ is a $C_1$ to $C_{10}$ alkyl, a $C_5$ to $C_{10}$ cycloalkyl, or piperidine radical of formula (II);

n is an integer from 2 to 6; and when n is 2, $R_3$ is a radical of formula (III)

wherein $R_6$, $R_7$, same or different, are hydrogen, $C_1$ to $C_{10}$ alkyl, $C_5$ to $C_{10}$ cycloalkyl, or a radical of formula (II), $R_8$ being a $C_2$ to $C_{10}$ alkylene, a $C_6$ to $C_{10}$ cycloalkylene, a $C_6$ to $C_{10}$ arylene or xylene, or $R_3$ is a 1,4-piperazinyl radical;

when n is 3 to 6, $R_3$ is a radical of formula (IV)

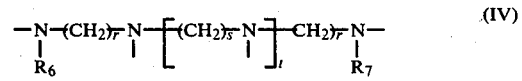

wherein $R_6$, $R_7$ are as above indicated, r, s, same or different, are an integer from 2 to 6 and t is 0 to 3;

in the formula (I) there is in at least one of the radicals $R_1X$—, $R_2X$—, $R_3$, at least one piperidine radical of formula (II) present.

2. A compound according to claim 1, wherein $R_1$, $R_2$ are $C_1$–$C_8$ alkyl, phenyl, 2,6-dimethylphenyl, 2,2,6,6-tetramethyl-4-piperidinyl, or 1,2,2,6,6-pentamethyl-4-piperidinyl; X is —O—,

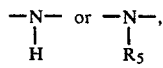
where $R_5$ is $C_1$ to $C_8$ alkyl; and n is 2 or 3;
when n is 2, $R_3$ is —NH—(CH$_2$)$_r$—NH— or
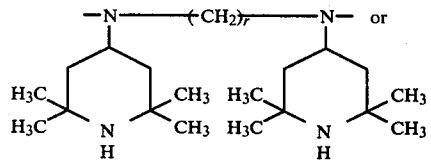
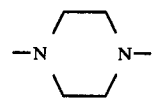
wherein r is an integer from 2 to 6;
when n is 3, $R_3$ is
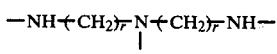
where r is 2 or 3.
3. A compound according to claim 1 of formula
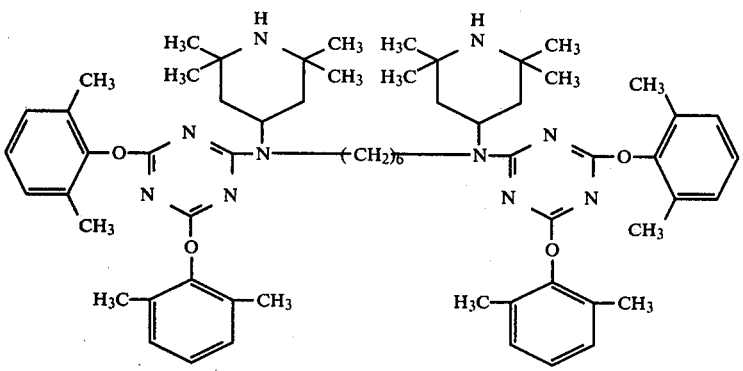
4. A compound according to claim 1 of formula
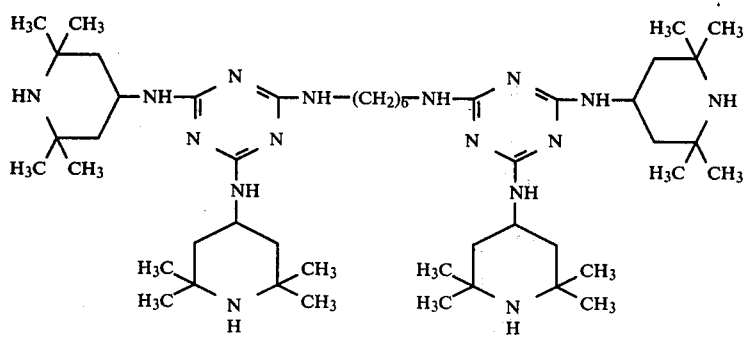
5. A compound according to claim 1 of formula
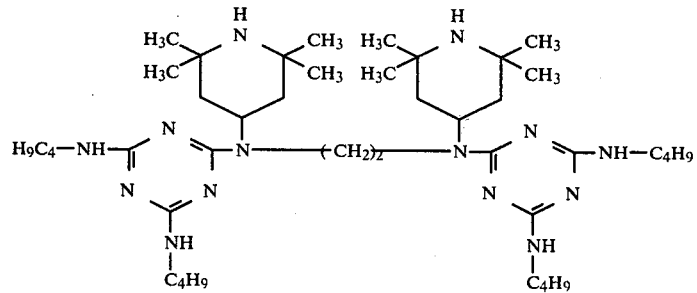
6. A compound according to claim 1 of formula

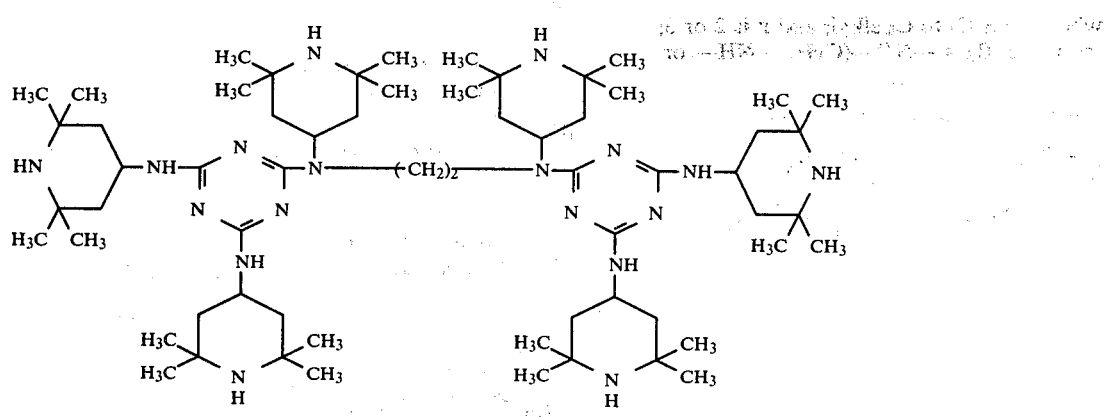
7. A compound according to claim 1 of formula
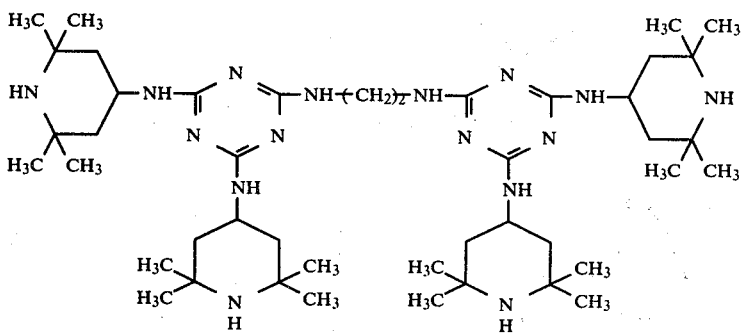
8. A compound according to claim 1 of formula
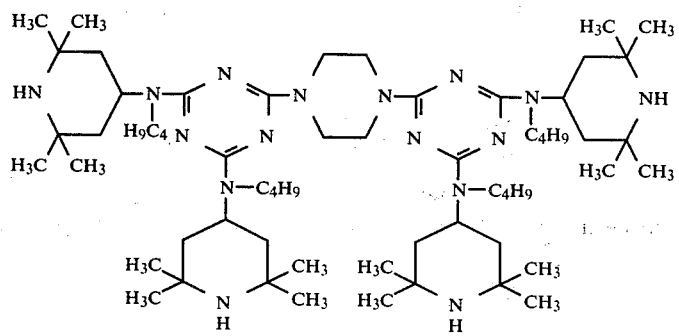
9. A compound according to claim 1 of formula